United States Patent
Xu et al.

(10) Patent No.: US 9,798,778 B2
(45) Date of Patent: Oct. 24, 2017

(54) SYSTEM AND METHOD FOR DYNAMIC GROWING OF A PATIENT DATABASE WITH CASES DEMONSTRATING SPECIAL CHARACTERISTICS

(75) Inventors: Ye Xu, Hartsdale, NY (US); Lilla Boroczky, Mount Kisco, NY (US); Mark Simpson, White Plains, NY (US)

(73) Assignee: Koninklijke Philips N.V., Eindhoven (NL)

( * ) Notice: Subject to any disclaimer, the term of this patent is extended or adjusted under 35 U.S.C. 154(b) by 309 days.

(21) Appl. No.: 13/880,200

(22) PCT Filed: Oct. 11, 2011

(86) PCT No.: PCT/IB2011/054478
§ 371 (c)(1),
(2), (4) Date: Apr. 18, 2013

(87) PCT Pub. No.: WO2012/052876
PCT Pub. Date: Apr. 26, 2012

(65) Prior Publication Data
US 2013/0208962 A1    Aug. 15, 2013

Related U.S. Application Data

(60) Provisional application No. 61/394,434, filed on Oct. 19, 2010.

(51) Int. Cl.
G06F 17/30 (2006.01)
G06F 19/00 (2011.01)
G06T 7/00 (2017.01)

(52) U.S. Cl.
CPC ...... *G06F 17/3053* (2013.01); *G06F 19/3443* (2013.01); *G06T 7/0014* (2013.01)

(58) Field of Classification Search
None
See application file for complete search history.

(56) References Cited

U.S. PATENT DOCUMENTS 5,878,746 A    3/1999   Lemelson et al.
6,006,191 A *  12/1999  DiRienzo ............. G06F 19/321
                                            705/2

(Continued)

FOREIGN PATENT DOCUMENTS

CN    101271489 A    9/2008
JP    2008234309 A   10/2008

(Continued)

OTHER PUBLICATIONS

Xu, Y et al. "Case-based clinical decision support for breast cancer diagnosis using dynamic contrast-enhanced MRI images", International Journal of Computer Assisted Radiology and Surgery, vol. 4, No. Suppl 1, Jun. 2009, pp. S175-S176.

(Continued)

*Primary Examiner* — Tsung-Yin Tsai

(57) ABSTRACT

A system and method for context-dependent data filtering for clinical decision support are disclosed. The system and method comprise determining values for characteristics of a present case, determining whether the present case is a special case based on the determined values, receiving input from a user verifying that the present case is the special case and saving the present case to a database containing a compilation of cases if the user verifies that the present case is the special case.

15 Claims, 6 Drawing Sheets

| Feature Name | Concept |
|---|---|
| RimOrSeptationRatio | Number of voxels of a dark region divided by the total number voxels in the lesion region |
| meanRimThickness | Mean of rim thickness |
| maxRimThickness | Maximum thickness of the rim |
| homoRatioB | Ratio of the mean intensity of black area to that of the white area |
| homoRatioF | Ratio of mean intensity of the white area to that of the black area |
| HeterNum | Number of dark regions |
| BlackAreaRatio | Ratio of the black area to the whole other area in the lesion |
| HeteNumberAdjusted | Number of dark regions, not counting very small dark regions (total number of voxels<3) |

(56) References Cited

U.S. PATENT DOCUMENTS

| | | | |
|---|---|---|---|
| 6,901,156 B2 * | 5/2005 | Giger | G06F 19/321 378/37 |
| 7,110,583 B2 | 9/2006 | Yamauchi | |
| 7,374,077 B2 | 5/2008 | Shimura | |
| 7,545,964 B2 | 6/2009 | Lang et al. | |
| 7,617,279 B2 | 11/2009 | Nakajima et al. | |
| 7,640,051 B2 | 12/2009 | Krishnan et al. | |
| 7,699,752 B1 * | 4/2010 | Anderson | A63B 24/0062 482/1 |
| 7,827,043 B2 | 11/2010 | Tahan | |
| 8,260,810 B2 | 9/2012 | Hisanaga et al. | |
| 8,600,133 B2 | 12/2013 | Buelow | |
| 8,718,341 B2 | 5/2014 | Buelow et al. | |
| 2002/0186818 A1 * | 12/2002 | Arnaud | G06T 7/80 378/165 |
| 2003/0069759 A1 * | 4/2003 | Smith | G06F 19/322 705/3 |
| 2004/0015372 A1 | 1/2004 | Bergman et al. | |
| 2004/0073486 A1 | 4/2004 | Kim | |
| 2005/0049497 A1 * | 3/2005 | Krishnan | G06F 19/321 600/437 |
| 2005/0201599 A1 | 9/2005 | Matsui | |
| 2006/0036619 A1 | 2/2006 | Fuerst et al. | |
| 2006/0200010 A1 | 9/2006 | Rosales et al. | |
| 2007/0025704 A1 * | 2/2007 | Tsukazaki | G06F 17/30017 386/230 |
| 2007/0092142 A1 | 4/2007 | Kuriathungal et al. | |
| 2007/0118399 A1 * | 5/2007 | Avinash | G06F 19/322 705/2 |
| 2008/0192995 A1 | 8/2008 | Zhao | |
| 2009/0076849 A1 * | 3/2009 | Diller | G06F 19/323 705/3 |
| 2009/0125555 A1 | 5/2009 | Stanis et al. | |
| 2009/0171871 A1 * | 7/2009 | Zhang | G06F 19/345 706/12 |
| 2010/0067219 A1 | 3/2010 | Tu et al. | |
| 2010/0086185 A1 * | 4/2010 | Weiss | B60R 25/00 382/131 |
| 2010/0228727 A1 | 9/2010 | Hisanaga et al. | |
| 2011/0123073 A1 * | 5/2011 | Gustafson | G06F 19/321 382/128 |
| 2013/0208962 A1 | 8/2013 | Xu et al. | |

FOREIGN PATENT DOCUMENTS

| | | |
|---|---|---|
| JP | 2010092413 A | 4/2010 |
| WO | 2009136354 A1 | 11/2009 |
| WO | 2010038172 A1 | 4/2010 |

OTHER PUBLICATIONS

Erguvan-Dogan Basak et al. "Bi-rads-MRI: a primer", American Journal of Roentgenology American Roentgen Ray Society, US, vol. 187, No. 2, Aug. 1, 2006, pp. W152-W160.

Wang, Y., "A research for the construction of synchronous medical image teaching system based on clinical data source", Chinese Masters Dissertations Full-text Database, information technology series, No. 12, 1138-378, Dec. 15, 2009.

Erguvan-Dogan, B. et al. Bi_Rads-MRI: a primer. American Journal of Roentgenology, Aug. 1, 2006 American, Roentgen Ray Society, US, Source info: vol. 187, Nr: 2, pp. W152-W160, 5,9,15,19.

* cited by examiner

| Feature Name | Concept |
|---|---|
| RimOrSeptationRatio | Number of voxels of a dark region divided by the total number voxels in the lesion region |
| meanRimThickness | Mean of rim thickness |
| maxRimThickness | Maximum thickness of the rim |
| homoRatioB | Ratio of the mean intensity of black area to that of the white area |
| homoRatioF | Ratio of mean intensity of the white area to that of the black area |
| HeterNum | Number of dark regions |
| BlackAreaRatio | Ratio of the black area to the whole other area in the lesion |
| HeteNumberAdjusted | Number of dark regions, not counting very small dark regions (total number of voxels<3) |

Fig. 7

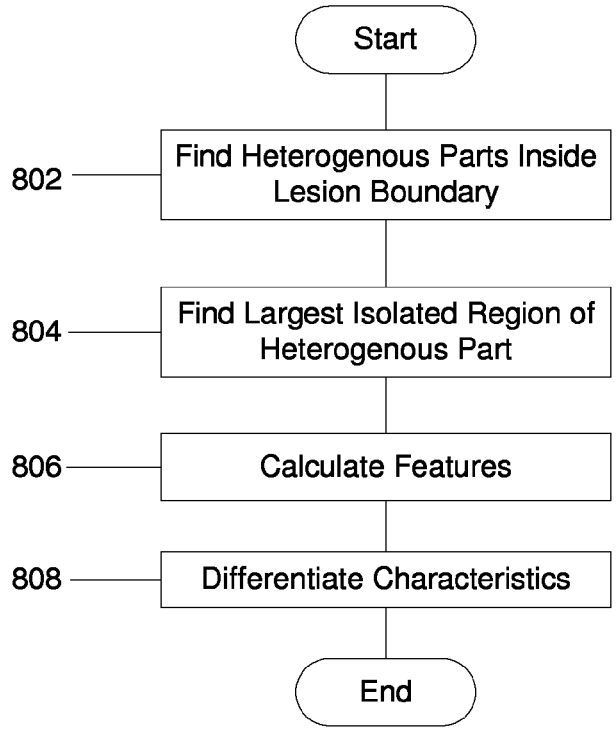

Fig. 8

SYSTEM AND METHOD FOR DYNAMIC GROWING OF A PATIENT DATABASE WITH CASES DEMONSTRATING SPECIAL CHARACTERISTICS

BACKGROUND

Breast cancer is one of the most common cancers and the second most frequent cause of cancer-related deaths among women in the United States. Dynamic Contrast-Enhanced MRI (DCE-MRI) screening is usually recommended in addition to mammography for high-risk women and it is increasingly used as a key staging tool for newly diagnosed breast cancer.

Clinical decision support (CDS) methods based on case-based reasoning (CBR) aid physicians' decision making by presenting previously diagnosed or treated cases that are similar to the case in question. A CBR-based CDS system will allow physicians to access a set of past cases that exceeds their own historical experience. For breast cancer diagnosis, it can aid in diagnostic interpretation of suspicious lesions with the potential to reduce unnecessary biopsies and delays in treatment. However, significant research challenges remain for CBR-based CDS for breast cancer.

SUMMARY OF THE INVENTION

A method for determining values for characteristics of a present case, determining whether the present case is a special case based on the determined values, receiving input from a user verifying that the present case is the special case and saving the present case to a database containing a compilation of cases if the user verifies that the present case is the special case.

A system having a memory storing a compilation of cases and a processing device determining values for characteristics of a present case and determining whether the present case is a special case based on the determined values, the processor further receiving input from a user verifying the present case is the special case and saving the present case to the memory if the user verifies that the present case is the special case.

A non-transitory computer readable storage medium storing a set of instructions executable by a processor. The set of instructions operable to determine values for characteristics of a present case, determine whether the present case is a special case based on the determined values, receive input from a user verifying that the present case is the special case and save the present case to a database containing a compilation of cases if the user verifies that the present case is the special case.

BRIEF DESCRIPTION OF THE DRAWINGS

FIG. 7 shows an exemplary table of new image features to be calculated to characterize lobular, rim enhancement, and dark internal septation lesion characteristics.

FIG. 8 shows an exemplary image processing method used to differentiate enhancement type.

DETAILED DESCRIPTION

Figure 1:
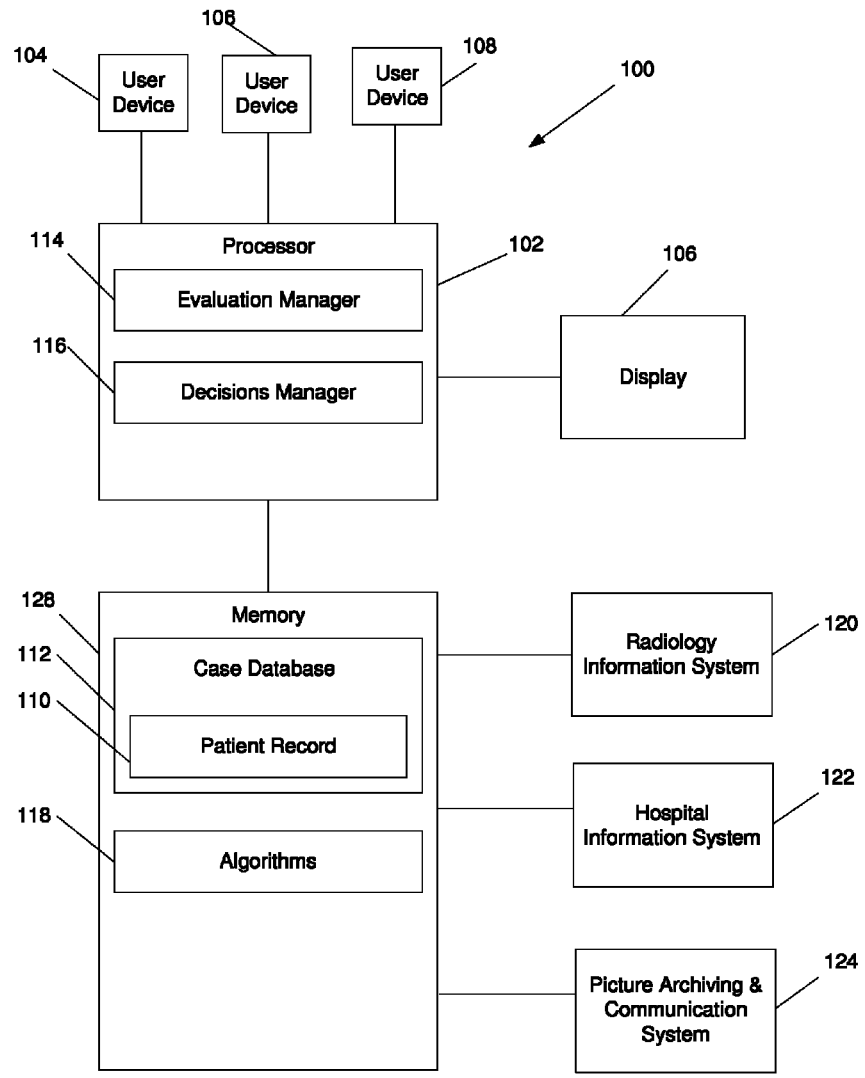
FIG. 1 shows a schematic diagram of a system according to an exemplary embodiment.

The exemplary embodiments may be further understood with reference to the following description and the appended drawings, wherein like elements are referred to with the same reference numerals. The exemplary embodiments relate to a context-dependent data filtering for a clinical decision support system and method. In particular, the exemplary embodiments provide a system and method for filtering patient data based upon the context in which a user is interacting with the system to provide only the most relevant data to the user. Although the exemplary embodiments are described with respect to a patient suffering from breast cancer, it will be understood by those of skill in the art that the systems and methods of the exemplary embodiments of the present invention may be used in any healthcare setting such as, for example, cardio informatics and disease management.

As shown in FIG. 1, a system 100 comprises a processing device 102 that is connected to a plurality of user devices 104-108 via a communications network such as, for example, a wired/wireless LAN/WAN, an intranet, the Internet, GPRS, mobile networks, etc. The processing device 102, as shown in FIG. 1, is a server comprising an evaluation manager 114 that performs calculations for each new case and a decision manager 116 that determines if the new case is a special case and, if so, provides a user (e.g., physician, administrator) with a recommendation to store the case.

The user devices 104-108 may be any wired or wireless computing devices that connect to and communicate with the processing device 102, e.g., portable computing device, personal digital assistant (PDA), laptop computer, tablet, notebook, etc. The user devices 104-108 may include a user interface for displaying the processed information to the user and permitting the user to input information to the processing device 102. For example, the user interface may be a graphical user interface displayed to the user on a display and permitting information to be entered via an input device. It will be understood by those of skill in the art that the system 100 may include any number of user devices 104-108.

The storage device 128 comprises a database 112 of past cases that have previously been saved. As will be described in greater detail below, the database 112 includes information of all the case in the database 112 (e.g., statistical information including mean, standard deviation, kurtosis, and other quantitative information, etc.) that is needed to analyze new and past cases (e.g. whether the case is typical or deviant). These values are based on the calculations performed by the evaluation manager 114 for all the cases in the database. The database 112 also includes a record 110 for every patient that has a case saved in the database 112. In order to perform calculations on a case, the evaluations manager 114 uses algorithms 118 which are stored in the storage device 128. To enable the dynamic growth of the database, the database 112 is further connected to other information systems such as the institution's Radiology Information System (RIS), Hospital Information System (HIS), and Picture Archiving and Communication System (PACS). The system 100 may also be incorporated into any case-based retrieval or CDS system.

The following provides an example of the functionality of the system 100 that is specific to breast cancer. However, as described above, those skilled in the art will understand that the functionality described herein for the system 100 is not limited to breast cancer evaluations. The functionality described herein may also be applicable to other medical conditions such as other types of cancer, cardiovascular disease, orthopedic issues, stroke, trauma, etc.

Figure 2:
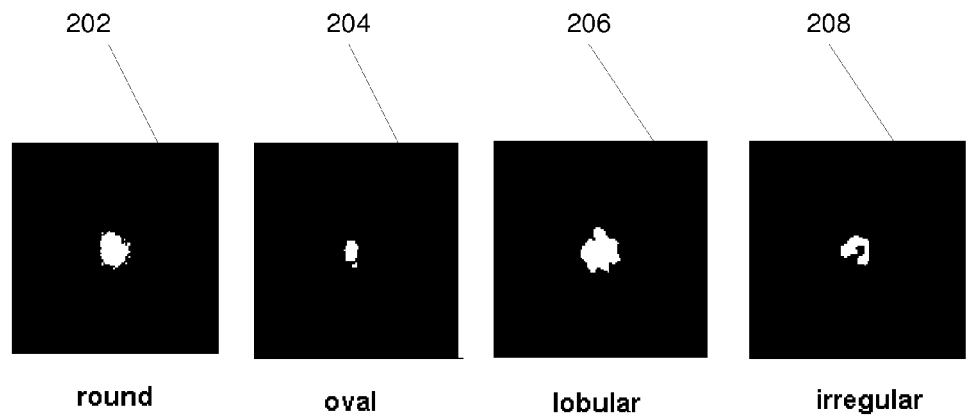
FIG. 2 shows four lesion shapes.
Figure 3:
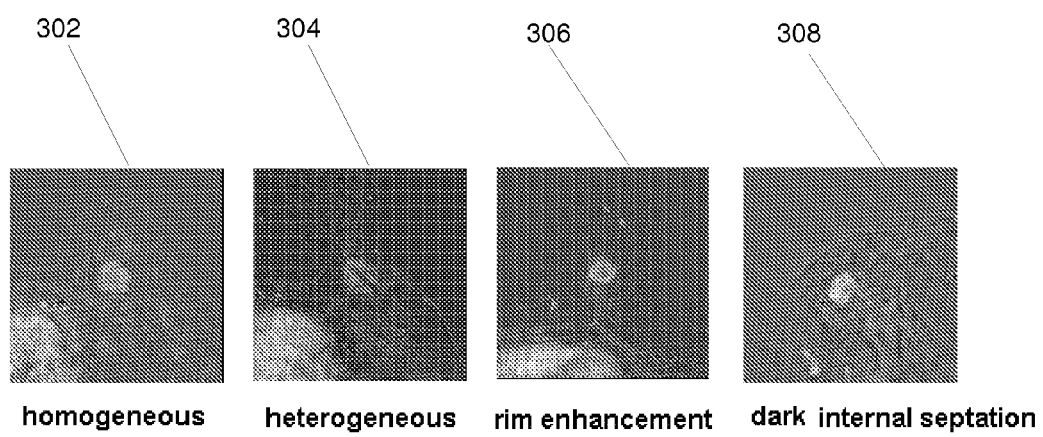
FIG. 3 shows four types of enhancement.

Returning to the breast cancer example, most of the qualitative characteristics of the morphologic description of breast lesions are calculated on shape, margin, and internal enhancement of the lesions. As shown in FIG. 2, shapes of lesions include round 202, oval 204, lobular 206, and irregular 208. Margins includes smooth, spiculated, and irregular shapes. A lesion with spiculated or irregular margin and shape tends to be a malignant lesion. As seen in FIG. 3, common internal enhancement of lesions includes homogeneous 302, heterogeneous 304, rim enhancement 306, and dark internal septation 308. If the intensities of the voxels in a lesion are different and enhancement is non-uniform, the enhancement tends to be more heterogeneous 304. Rim enhancement 306 of breast lesions of MR imaging is due to a combination of angiogenesis, distribution, and the degree of fibrosis. This results in a "black hole" of cell death. The thicker the rim (the white area of the lesion), the more likely the lesion is malignant. The appearance of rim enhancement showed a statistically significant association with malignant lesions and is a very useful indicator of the malignancy of the lesions. Dark internal septations 308 refer to non-enhancing septations in an enhancing mass. These look like black lines inside the lesion. They are typical of fibroadenomas, especially when the lesion has smooth margin or lobulated shape. The presence of internal septations and lobular shape is found to be highly predictive of benignity.

Each of these qualitative characteristics of the breast lesions may be assigned a quantitative value based on an appropriate scale. One exemplary scale may include a higher score for a qualitative characteristic that is more indicative of malignancy and a lower score for a qualitative characteristic that is more indicative of a benign lesion. However, any appropriate scale to assign quantitative values may be used. The calculations performed by the evaluation manager to assign the quantitative values are described in greater detail below.

Figure 4:
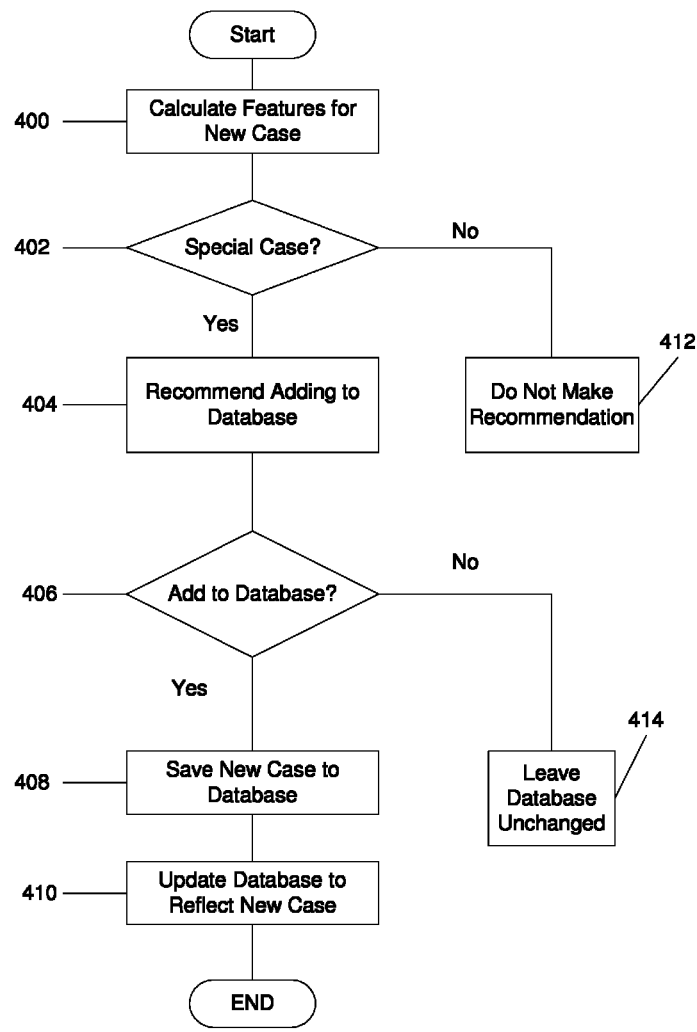
FIG. 4 shows a flow diagram of a user-system method according to an exemplary embodiment.

FIG. 4 shows an exemplary process carried out by the processing device 102 when a new case is presented to it. In step 400, the processor calculates values for the lesion characteristics described above with respect to FIGS. 2 and 3. Based on these values, the processor determines, at step 402, whether or not the present case is a special case (i.e. a case that would be beneficial to future diagnoses). If the present case does not have special characteristics, the decisions manager 116 does not make any recommendations to the user (step 412). However, if the processor determines that the present case is a special case, the decision manager 116 recommends saving the present case to the database 112, at step 404. For example, the user devices 104-108 may include an application or a program that interfaces with the processor 102 such that the recommendation is sent from the processor 102 to the user devices 104-108 and is presented to the user on a user interface of the application displayed on a display screen of the user devices 104-108. The decision to save the present case to the database 112 then lies with the user (step 406). Via the user interface presented on the user device 104-108, the user may enter a selection of whether or not to save the case to the database 112. If the user does not wish to save the present case to the database, no changes are made to the database 112 (step 414).

If the user decides to save the present case, the case is added to the database 112 (step 408) for future retrieval and the database 112 is updated to reflect the addition of the new case (step 410). When a case is added to the database 112, both the image of the lesion and the calculated values are added. In addition, other identifying data for the case may also be added to the database 112 such as patient ID, sex, age, presenting date, family history, medical history, co-morbidities, diagnosis, treatments administered, etc. Any information that may be used to retrieve the case at a later time may be added to the database 112. Furthermore, the updating of the database also includes recalculation or reapplying machine learning methods, such as artificial neural network for any or all of the parameters associated with the database such as the statistical parameters as a result of the adding of the new case to the database 112.

It should be noted that the decision manager 116 may use general criteria for determining a special case or may also use individualized criteria based on a specific user (e.g., physician). More specifically, an individual user may have their own criteria for determining whether a case is a special case that they want to include in the database 112. In such a situation, the user may identify to the decision manager 116 or provide criteria to the decision manager 116 those qualitative and/or quantitative characteristics that the user finds important. When the decision manager 116 identifies these characteristics in a new case, the decision manager 116 will make the recommendation to the user such as described in step 404 above. However, the decision manager 116 may also include generalized criteria (e.g., statistical criteria, classification criteria, etc.) that may be used by any number of users in order to identify special cases to be included in the database 112. One example of statistical criteria may be the mean of rim thickness being greater than a pre-set value. However, those skilled in the art will understand that there are many more examples of statistical criteria and other types of machine learning techniques that may be used.

In addition, a user may have an individualized database 112 or may use a general database 112. For example, a user may decide that they are only interested in looking at cases that they have identified as special for helping in future diagnoses. In such a situation, the system 100 may include an individualized database 112 that is specific to that user that is only populated with cases by that user. The individualized database 112 may also include other users' cases that were added by the first user. That is, the decision manager 116 may identify another user's case that may be interesting to the specific user and give the user the option of adding that case to the individualized database 112. In the case of the general database 112, the users are adding cases that may be retrieved by all users of the system 100.

Figure 5:
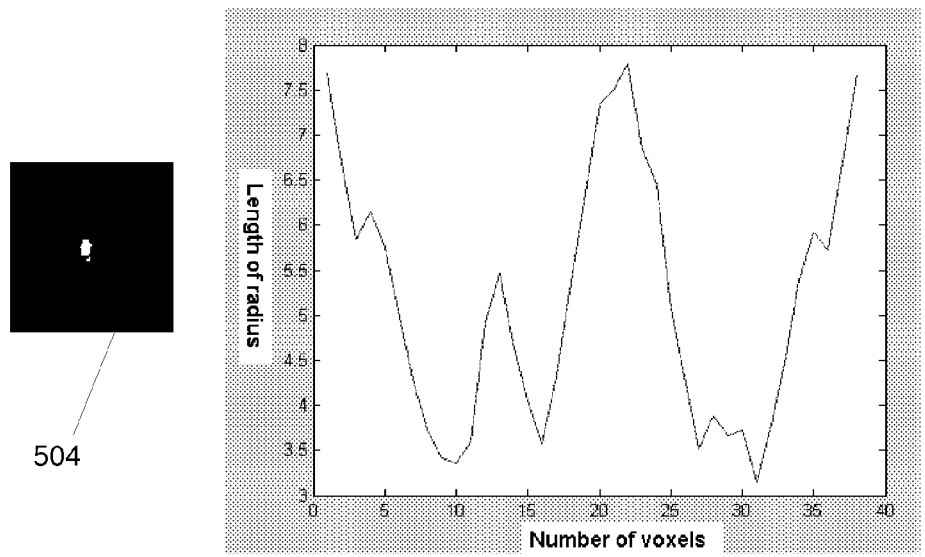
FIG. 5 shows an oval-shaped lesion (left) and its radius distribution (right).
Figure 6:
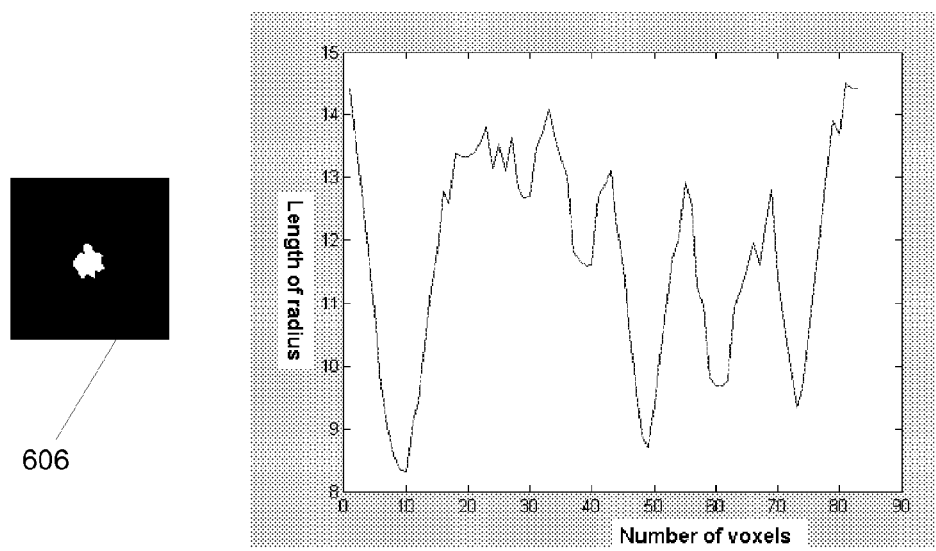
FIG. 6 shows a lobular-shaped lesion (left) and its radius distribution (right).

An exemplary calculation performed by the evaluation manager 114 on a new case will now be described. It is noted that the example calculation provided below is based on a morphological feature. However, it should be understood that similar calculations may be performed using non-image based features. Specifically, the features of interest may include any feature that the radiologist deems important, including non-morphological features such as genetics, family history, epidemiology, etc. For the purposes of providing an example calculation, a morphological feature will be selected. When a new case is presented to the processing device 102, the shape of the lesion is determined. To distinguish lobular shapes from the other shapes, the evaluation manager 114 calculates the distance from each voxel on the surface of the lesion to the center of the lesion. Based on the calculated distance (radius), an array is generated. Other features, not described here, are calculated based on this array. As seen in FIGS. 5 and 6, the radii of the oval lesion have less variance than that of the lobular lesion because the oval lesion does not have as many leaves as the lobular shaped lesion. The evaluation manager 114 then determines the local maximum and local minimum of the array of radii. As seen in FIGS. 5 and 6, the total number of local maximums of the lobular lesion is greater than that of the oval shaped lesion. Furthermore, although the total number of local maximums of the irregular shaped lesion might be similar to that of the lobular shaped lesion, the variance of the local maximum and minimum of the lobular shaped lesion would most likely be less than that of the irregular shape. These features are independent of the size of the lesion. FIG. 7 shows examples of the different features calculated for each new case presented to the processing device 102 in the case of breast cancer lesions.

After the shape and above-mentioned characteristics of the lesion are determined, the evaluation manager 114 characterizes the enhancement of the lesion in the present case. An exemplary simplified algorithm for this characterization is shown in FIG. 8. To characterize the rim enhancement and dark internal septation, the evaluation manager 114 first finds the lesion boundary and identifies heterogeneous regions (dark regions) inside the lesion. To differentiate between a white region and a black region, an iterative method is used to find a threshold value. Next, the largest isolated heterogeneous region, which is shown as a "black hole" of dead cells, is found. The boundary of this dark region is then found. The rim is the entire lesion minus the largest dark region, which is shown as a white area of the lesion. During this process, the features listed in FIG. 7 are calculated. RimOrSeptationRatio is used to differentiate between rim enhancement and dark internal septation. Features starting with "homo" and "hetero" are used to differentiate between homogeneous regions and heterogeneous regions.

Figure 9:
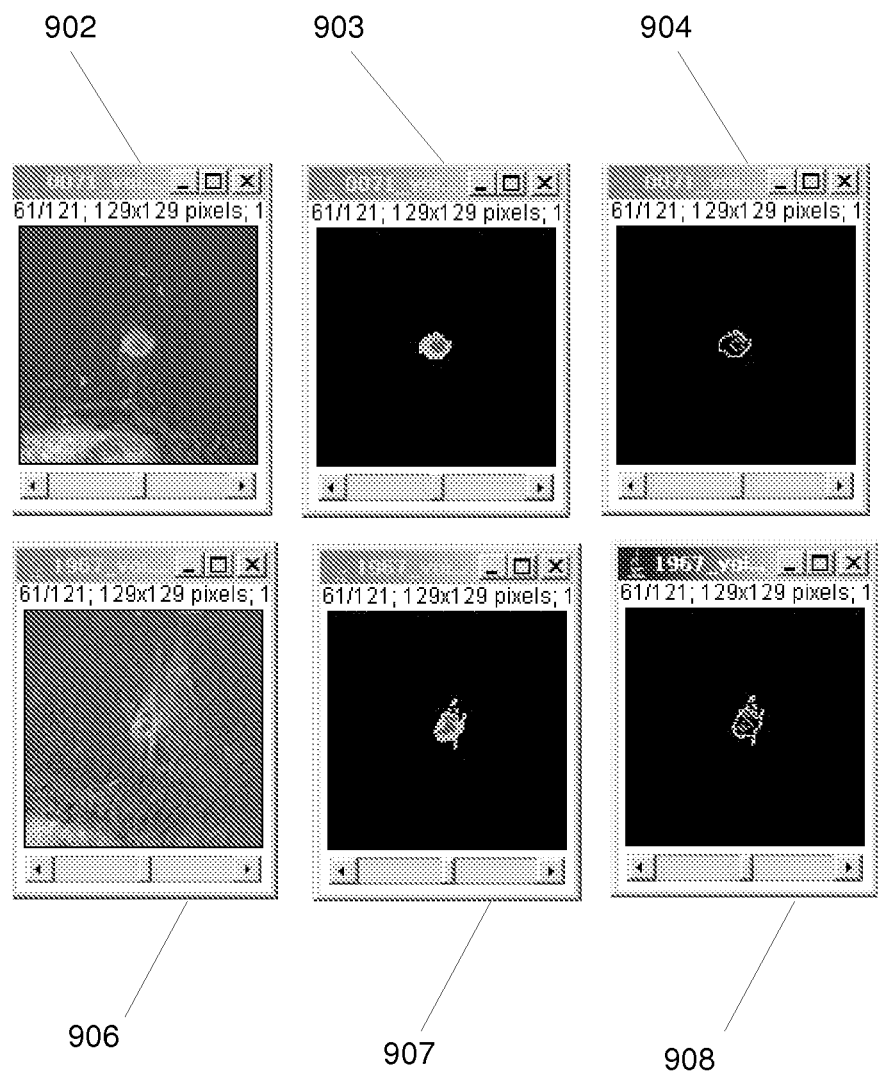
FIG. 9 shows an exemplary image processing for the two cases with rim enhancement.

FIG. 9 shows the result of the image processing of the two lesions with rim enhancement. The left column shows the original images 902 and 906. The middle column shows the images 903 and 907 after finding the inner "black holes," the rim is the white area inside the lesion. The right column images 904 and 908 has the gray edge showing the boundary of the "black hole" and the white edge showing the lesion boundary.

In another embodiment, during the automatic calculations of the features of a newly presented case, the processing device 102 can retrieve past cases with similar special characteristics to the present case. As described above, one of the reasons for saving cases to the database 112 is so that users may retrieve the case at a later time to aid in new diagnoses. Thus, when a new case is presented and its values calculated, one or more saved cases with similar values may be retrieved. The other identifying information that is stored for the saved cases (e.g., sex, age, etc.) may also be used by the physician to discriminate between the retrieved cases. For example, if the system 100 retrieves six similar cases, the physician may only desire to see those cases that are for a female over the age of 40. The identifying information may then also be used to retrieve the actual images for the saved cases. This retrieval can be from at least one of the RIS 120, HIS 122, and PACS 124 connected or included in the storage device 128.

Those skilled in the art will understand that the above-described exemplary embodiments may be implemented in any number of manners, including, as a separate software module, as a combination of hardware and software, etc. For example, the evaluation manager 114 and the decision manager 116 may be programs containing lines of code that, when compiled, may be executed on a processor. The programs may be embodied on a non-transitory computer readable storage medium.

It is noted that the claims may include reference signs/numerals in accordance with PCT Rule 6.2(b). However, the present claims should not be considered to be limited to the exemplary embodiments corresponding to the reference signs/numerals.

It will be apparent to those skilled in the art that various modifications may be made to the disclosed exemplary embodiments and methods and alternatives without departing from the spirit or scope of the disclosure. Thus, it is intended that the present disclosure cover modifications and variations provided that they come within the scope of the appended claims and their equivalents.

What is claimed is:
1. A method, comprising:
receiving, by a user interface, criteria for determining whether a present case is a special case, the criteria comprising qualitative characteristics and quantitative values corresponding to at least some of the qualitative characteristics,
wherein the present case comprises at least one medical image;
determining, by a computer processor, at least one quantitative value corresponding to at least one qualitative characteristic of the present case,
wherein the at least one qualitative characteristic of the present case relates to at least one morphological feature of the at least one medical image, and the at least one quantitative value relates to at least one measurement of the at least one morphological feature;
determining, by the computer processor, whether the present case is the special case by:
comparing the at least one qualitative characteristic and determined at least one quantitative value of the present case to the criteria, and
comparing the determined at least one quantitative value to a statistical significance threshold,
wherein the statistical significance threshold comprises a predetermined value;
receiving input from the user verifying that the present case is the special case; and
when the user verifies that the present case is the special case, saving the present case, including contents of the present case, to a database containing a compilation of cases, the database comprising an individualized database and a general database,
wherein the present case is saved to the individualized database only when the at least one qualitative characteristic and determined at least one quantitative value match or exceed the criteria,
wherein the present case is saved to the general database only when the determined at least one quantitative value matches or exceeds the statistical significance threshold.
2. The method of claim 1, further comprising:
updating the database to reflect the addition of the present case.

3. The method of claim 2, wherein the updating includes one of updating statistical values of the compilation of cases and applying machine learning techniques to reflect the values of the present case.

4. The method of claim 1, wherein the present case includes a medical image, the medical image being stored in a separate database, wherein the medical image may be retrieved from the separate database based on one of the calculated values and patient information.

5. The method of claim 1, further comprising:
selecting the characteristics of the present case, the selection including one of morphological and non-morphological characteristics for a medical image.

6. The method of claim 5, further comprising:
calculating, when the selected characteristic is a shape of a lesion in the medical image, a distance from each voxel on a surface of the lesion to a center of the lesion; and
determining, when the selected characteristic is an enhancement characteristic of a lesion, a rim of the lesion by finding a boundary of the lesion and identifying heterogeneous regions inside the lesion.

7. The method of claim 1, further comprising:
retrieving at least one case from the compilation of cases based on the determined quantitative values and patient information of the present case compared with the quantitative values and patient information of each of the compilation of cases.

8. The method of claim 1, wherein the determining whether the present case is the special case further includes one of analyzing statistical criteria of the determined values, analyzing statistical criteria of the compilation of cases in the database and applying machine learning techniques to the present case and the compilation of cases.

9. A system, comprising:
a non-transitory memory storing an individualized database comprising a compilation of cases and a general database comprising a compilation of cases; and
a processing device
receiving criteria for determining whether a present case is a special case, the criteria comprising qualitative characteristics and quantitative values corresponding to at least some of the qualitative characteristics,
wherein the present case comprises at least one medical image;
determining at least one quantitative value corresponding to at least one qualitative characteristic of the present case,
wherein the at least one qualitative characteristic of the present case relates to at least one morphological feature of the at least one medical image, and the at least one quantitative value relates to at least one measurement of the at least one morphological feature;
determining whether the present case is the special case by comparing the at least one qualitative characteristic and determined at least one quantitative value of the present case to the criteria, and comparing the determined at least one quantitative value to a statistical significance threshold,
wherein the statistical significance threshold comprises a predetermined value;
receiving input from the user verifying the present case is the special case and, when the user verifies that the present case is the special case, saving the present case, including contents of the present case, to the non-transitory memory,
wherein the present case is saved to the individualized database only when the at least one qualitative characteristic and determined at least one quantitative value match or exceed the criteria,
wherein the present case is saved to the general database only when the determined at least one quantitative value matches or exceeds the statistical significance threshold.

10. The system of claim 9, further comprising:
a further non-transitory memory storing a plurality of medical images, wherein the present case includes a medical image, the medical image being stored in the further non-transitory memory, wherein the medical image may be retrieved from the further non-transitory memory based on one of the calculated values and patient information.

11. The system of claim 10, wherein the further non-transitory memory comprises one of a radiology information system, a hospital information system, and a picture archiving and communication system.

12. The system of claim 9, wherein the processing device further receives a selection of the characteristics of the present case, the selection including one of morphological and non-morphological characteristics of a medical image.

13. The system of claim 12, wherein the processing device calculates, when the selected characteristic is a shape of a lesion in the medical image, a distance from each voxel on a surface of the lesion to a center of the lesion, the processor further calculating, when the selected characteristic is an enhancement characteristic of a lesion, a rim of the lesion by finding a boundary of the lesion and identifying heterogeneous regions inside the lesion.

14. The system of claim 9, wherein the processing device further retrieves at least one case from the compilation of cases based on the determined quantitative values and patient information of the present case compared with the quantitative values and patient information of each of the compilation of cases.

15. The system of claim 9, wherein the processing device, when determining whether the present case is the special case, performs one of analyzing statistical criteria of the determined values, analyzing statistical criteria of the compilation of cases in the database and applying machine learning techniques to the present case and the compilation of cases.

* * * * *